United States Patent
Reinicker et al.

(10) Patent No.: US 10,221,201 B2
(45) Date of Patent: Mar. 5, 2019

(54) TIN-CONTAINING DOPANT COMPOSITIONS, SYSTEMS AND METHODS FOR USE IN ION IMPLANTATION SYSTEMS

(71) Applicants: Aaron Reinicker, Buffalo, NY (US); Ashwini K. Sinha, East Amherst, NY (US); Qiong Guo, Clarence, NY (US)

(72) Inventors: Aaron Reinicker, Buffalo, NY (US); Ashwini K. Sinha, East Amherst, NY (US); Qiong Guo, Clarence, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 15/386,308

(22) Filed: Dec. 21, 2016

(65) Prior Publication Data

US 2017/0190723 A1 Jul. 6, 2017

Related U.S. Application Data (60) Provisional application No. 62/273,642, filed on Dec. 31, 2015.

(51) Int. Cl.
| | |
|---|---|
| *C07F 7/22* | (2006.01) |
| *C09D 5/24* | (2006.01) |
| *H01L 21/265* | (2006.01) |
| *C23C 14/48* | (2006.01) |
| *H01J 37/317* | (2006.01) |

(52) U.S. Cl.
CPC ............ *C07F 7/2208* (2013.01); *C09D 5/24* (2013.01); *C23C 14/48* (2013.01); *H01J 37/317* (2013.01); *H01L 21/26513* (2013.01); *H01L 21/26546* (2013.01)

(58) Field of Classification Search
USPC .................................. 250/482, 489
See application file for complete search history.

(56) References Cited

U.S. PATENT DOCUMENTS

| | | | |
|---|---|---|---|
| 3,472,694 A * | 10/1969 | Hanak | ..... C23C 16/14 257/E39.001 |
| 3,677,814 A | 7/1972 | Gillery | |
| 5,654,457 A | 8/1997 | Bergfried et al. | |
| 5,937,895 A | 8/1999 | Le Febre et al. | |
| 6,006,796 A | 12/1999 | Baker et al. | |

(Continued)

FOREIGN PATENT DOCUMENTS

| | | |
|---|---|---|
| EP | 3125274 A1 | 2/2017 |
| GB | 2033357 A | 5/1980 |

(Continued)

*Primary Examiner* — Phillip A Johnston
(74) *Attorney, Agent, or Firm* — Nilay S. Dalal (57) ABSTRACT

A novel method and system for using certain tin compounds as dopant sources for ion implantation are provided. A suitable tin-containing dopant source material is selected based on one or more certain attributes. Some of these attributes include stability at room temperature; sufficient vapor pressure to be delivered from its source supply to an ion chamber and, the ability to produce a suitable beam current for ion implantation to achieve the required implant Sn dosage. The dopant source is preferably delivered from a source supply that actuates under sub atmospheric conditions to enhance the safety and reliability during operation.

26 Claims, 3 Drawing Sheets

Schematic of beamline ion implant system (56) References Cited

U.S. PATENT DOCUMENTS

| | | | |
|---|---|---|---|
| 6,007,609 A | 12/1999 | Semerdjian et al. | |
| 6,045,115 A | 4/2000 | Martin, Jr. et al. | |
| 6,959,724 B2 | 11/2005 | Heiderman | |
| 7,708,028 B2* | 5/2010 | Brown | F16K 1/305 |
| | | | 137/494 |
| 7,905,247 B2 | 3/2011 | Campeau | |
| 8,110,815 B2* | 2/2012 | Sinclair | C23C 14/228 |
| | | | 250/425 |
| 9,064,795 B2* | 6/2015 | Koo | C23C 14/48 |
| 9,138,720 B2 | 9/2015 | Kim et al. | |
| 9,165,773 B2* | 10/2015 | Sinha | H01L 21/265 |
| 9,427,722 B2 | 8/2016 | Weston et al. | |
| 9,897,257 B2* | 2/2018 | Despres | F17C 13/04 |
| 2006/0093754 A1* | 5/2006 | Krueger | C23C 14/48 |
| | | | 427/523 |
| 2014/0329025 A1 | 11/2014 | Cleary et al. | |
| 2015/0056380 A1 | 2/2015 | Savas et al. | |
| 2015/0248992 A1 | 9/2015 | Sinha et al. | |
| 2016/0151762 A1 | 6/2016 | Fuller et al. | |
| 2016/0160348 A1 | 6/2016 | Siu et al. | |
| 2017/0122496 A1* | 5/2017 | Scannell | F17C 13/04 |

FOREIGN PATENT DOCUMENTS

| | | |
|---|---|---|
| JP | S60056066 A | 4/1985 |
| WO | 2015146749 A1 | 10/2015 |

* cited by examiner

Figure 1: Schematic of beamline ion implant system

Figure 2: Schematic of plasma immersion ion implant system

Figures 3a and 3b: Package for Sn dopant materials

Figures 4a, 4b, 4c: Examples of storage and delivery package for three separate states of Sn dopant source

| CAS Number | CAS Index Name | Formula | Vapor Pressure at 25 °C in Torr |
|---|---|---|---|
| 3582-18-1 | Stannane, trifluoromethyl- (9CI) | $F_3SnCH_3$ | 1280 |
| 51105-30-7 | Stannane, ethenyltrifluoro- | $F_3SnCH=CH_2$ | 499 |
| 65059-36-1 | Stannane, dimethylbis(trifluoromethyl)- | $(CH_3)_2Sn(CF_3)_2$ | 449 |
| 51105-29-4 | Stannane, ethyltrifluoro- | $F_3SnCH_2CH_3$ | 382 |
| 754-25-6 | Stannane, trimethyl(trifluoromethyl)- | $(CH_3)_3SnCF_3$ | 115 |
| 812-35-1 | Stannane, trimethyl(1,1,2,2,2-pentafluoroethyl)- | $(CH_3)_3SnCF_2CF_3$ | 84 |
| 815-22-5 | Stannane, trimethyl(1,2,2-trifluoroethenyl)- | $(CH_3)_3SnCF=CF_2$ | 66.3 |
| 649-48-9 | Stannane, diethyldifluoro- | $F_2Sn(CH_2CH_3)_2$ | 49.5 |
| 51105-28-3 | Stannane, butyltrifluoro- | $F_3SnCH_2CH_2CH_2CH_3$ | 38.8 |
| 594-27-4 | Stannane, tetramethyl | $Sn(CH_3)_4$ | 120 |
| 41268-44-4 | Stannane, tetrakis (trifluoromethyl) | $Sn(CF_3)_4$ | 1930 |
| 7646-78-8 | Stannane, tetrachloro | $Sn(Cl)_4$ | 20 |
| 1066-99-5 | Stannane, dimethoxy dimethyl | $(CH_3)_2Sn(OCH_3)_2$ | 45 |
| 1070-81-1 | Stannane, Ethoxy trimethyl | $(CH_3)_3SnOCH_2CH_3$ | 20 |
| 1066-58-6 | Stannane, Methoxy Trimethyl | $(CH_3)_3SnOCH_3$ | 60.1 |
| 185839-03-6 | Stannane, Dichloromethoxymethyl | $CH_3SnCl_2OCH_3$ | 23.7 |

Figure 5: Table Sn containing dopant sources

TIN-CONTAINING DOPANT COMPOSITIONS, SYSTEMS AND METHODS FOR USE IN ION IMPLANTATION SYSTEMS

This application claims priority to U.S. Provisional Patent application Ser. No. 62/273,642 filed Dec. 31, 2015, the disclosure of which is hereby incorporated by reference in its entirety.

FIELD OF INVENTION

The present invention relates to novel tin dopant compositions and delivery systems and methods of use for ion implantation systems.

BACKGROUND OF THE INVENTION

Ion implantation is utilized in the fabrication of semiconductor based devices such as Light Emitting Diodes (LED), solar cells, and Metal Oxide Semiconductor Field Effect Transistors (MOSFETs). Ion implantation is used to introduce dopants to alter the electronic or physical properties of semiconductors.

In a traditional ion implantation system, a gaseous species often referred to as the dopant source is introduced in to the arc chamber of an ion source. The ion source chamber comprises a cathode which is heated to its thermionic generation temperature to generate electrons. Electrons accelerate towards the arc chamber wall and collide with the dopant source gas molecule present in the arc chamber to generate a plasma. The plasma comprises dissociated ions, radicals, and neutral atoms and molecules of the dopant gas species. The ions are extracted from the arc chamber and then separated to pick a desired ionic species which is then directed towards the target substrate.

Tin (Sn) is recognized as a dopant with many uses. For example, tin (Sn) has emerged as a suitable dopant in germanium (Ge) to create strain in Ge and improve the flow of electrons and holes through Ge in a transistor. Additionally, Sn has also been explored as an active dopant species for III-V semiconductor devices.

Sn has been used in semiconductor devices. Sn can function in various ways, including as a gate oxide and gate electrode metal in metal-oxide-semiconductor field-effect transistors (MOSFETs); a dopant in copper (Cu) interconnects to prevent electro migration; and as an intrinsic getter in silicon (Si). Sn is generally deposited on a substrate using Physical Vapor Deposition (PVD) or Chemical Vapor Deposition (CVD). In PVD, Sn metal is heated in vacuum using an electron beam to heat a crucible of Sn or a Sn-containing compound. As the crucible temperature increases, the vapor pressure of Sn in the crucible increases and Sn vapor deposits on a substrate. CVD is a similar technique except the dopant source is a volatile Sn compound and will react with the substrate when deposited therein.

For example, mixtures of $Sn(CH_3)_4$ with either $CF_3I$ or $CF_3Br$ compounds can be co-deposited with $O_2$ at elevated temperatures on a heated substrate to produce films of $SnO_2$. Sn can also be embedded in the surface of a substrate using ion implantation. In one method of ion implantation, Sn metal is placed in close proximity to a filament and the temperature of the filament is high enough that radiative heating causes Sn to evaporate and collide with electrons to create Sn ions for doping. However, this method can cause Sn to deposit on the chamber walls or on the filament, shortening the filament lifetime.

There is no currently viable Sn dopant source available today for ion implantation. For these reasons, there is an unmet need for a Sn dopant source that can be used in traditional ion implantation systems.

SUMMARY OF THE INVENTION

The invention relates, in part, to certain tin dopant sources that are stable at room temperature, have sufficient vapor pressure and are capable of producing a sufficient beam current for ion implantation. The dopant source is preferably delivered in sub atmospheric conditions to enhance the safety and reliability during tin ion implantation.

In a first aspect, a method for using Sn containing dopant material for an ion implantation process, comprising the steps of: storing a Sn containing dopant source in a storage and delivery container; the Sn-containing dopant source characterized by one or more of the following attributes: (i) stability during storage and delivery; (ii) a vapor pressure of greater than or equal to 20 Torr at room temperature (25° C.); (iii) generation of an ion beam capable of doping greater than $10^{11}$ atoms/cm$^2$; (iv) naturally occurring as a liquid at room temperature; and (v) comprising Sn, H and a halogen atom; withdrawing the Sn containing dopant source in the vapor phase from the storage and delivery container; flowing the vaporized the Sn containing dopant source; and introducing the Sn-containing dopant source vapor to an ion source chamber.

In a second aspect, a source supply for a Sn dopant gas composition comprising: a Sn-containing dopant source composition characterized by one or more of the following attributes: (i) stability during storage and delivery; (ii) a vapor pressure of greater than or equal to 20 Torr at room temperature (25° C.); (iii) generation of an ion beam capable of doping greater than $10^{11}$ atoms/cm$^2$; (iv) naturally occurring as a liquid at room temperature; and (v) comprising Sn, H and a halogen atom; a delivery and storage device for maintaining the Sn-containing dopant source in a pressurized state within an interior volume of the device, said delivery device in fluid communication with a discharge flow path, wherein said delivery device is actuated to allow a controlled flow of the Sn-containing dopant source from the interior volume of the device in response to a sub-atmospheric condition achieved along the discharge flow path.

In a third aspect, a Sn-containing dopant composition for use in an ion implantation process, comprising: a Sn-containing dopant gas source material, source characterized by one or more of the following attributes: (i) stability during storage and delivery; (ii) a vapor pressure of greater than or equal to 20 Torr at room temperature (25° C.); (iii) generation of an ion beam capable of doping greater than $10^{11}$ atoms/cm$^2$; (iv) naturally existing as a liquid at room temperature; and (v) comprising Sn, H and a halogen atom.

BRIEF DESCRIPTION OF THE DRAWINGS

The objectives and advantages of the invention will be better understood from the following detailed description of the preferred embodiments thereof in connection with the accompanying figures wherein like numbers denote same features throughout and wherein.

DETAILED DESCRIPTION OF THE INVENTION

"Sn dopant gas composition", "Sn dopant source(s)", "Sn containing specie(s)" and "Sn-containing dopant source(s)" are used interchangeably herein and are intended to have the same meaning of specific tin compounds and materials selected based on certain criteria for improved Sn ion implantation. Unless indicated otherwise, all percentages are based on volume.

The present disclosure relates to a selection of suitable Sn dopant sources for ion implantation. The disclosure is set out herein in various embodiments, and with reference to various features and aspects of the invention. The disclosure contemplates some or all of such features, aspects and embodiments in various permutations and combinations, as well as elements and components thereof being aggregated to constitute various further implementations of the invention, as being within the scope of the disclosure. The disclosure may therefore be specified as comprising, consisting or consisting essentially of, any of such combinations and permutations of these specific features, aspects and embodiments, or a selected one or ones thereof.

The Sn compositions and compounds of the disclosure may be further described in particular embodiments by specific characteristics, conditions, structures, as applicable, in relation to various exemplifications thereof set forth herein.

The ion implantation methods and storage/delivery systems of the disclosure as a result of using such Sn compositions and compounds achieve improved ion source performance in relation to conventional Sn sources.

The present invention recognizes that today's Sn dopant sources have numerous shortcomings. For example, stannanes such as $SnH_4$ and $Sn_2H_6$ are commonly known Sn-containing gas compounds that could be used as a Sn dopant source, but these compounds are unstable and even at 25° C. can decompose into Sn metal and $H_2$ gas. Fluorides such as $SiF_4$ and $GeF_4$ are dopant source gases currently in use for Si and Ge ion implantation, but analogues for Sn such as $SnF_2$ and $SnF_4$ are solids with a melting point exceeding 200° C. The present invention recognizes and appreciates that such conventional materials when used as a dopant source for ion implantation pose a problem as these solids require significant heat to generate a vapor flux necessary for ion implantation and all flow lines in the system would have to be heated to prevent condensation of the dopant.

In view of these shortcomings, the disclosure in one aspect relates to a selection of certain Sn dopant sources that have at least one or more of the following attributes: (i) stability during storage and delivery; (ii) a vapor pressure of greater than or equal to 20 Torr at room temperature (25° C.); and (iii) generation of an ion beam capable of doping greater than $10^{11}$ atoms/cm$^2$. In addition to or as an alternative to some or all of such attributes, the disclosure in another aspect relates to a Sn dopant source that has at least one or more of the following attributes: (i) chemical stability during storage and delivery; (ii) naturally occurring as a liquid at room temperature; (iii) sufficient vapor pressure for delivery and processing in an ion implantation system; (iv) feasible synthesis routes; and (v) comprises Sn, H and a halogen atom. The various embodiments relating to such aspects will be discussed in connection with FIG. 5, which lists a table of specific Sn dopant sources for ion implantation as selected by the Applicants. Each of the species listed has a vapor pressure greater than or equal to 20 Torr and does not decompose at 25° C.

One embodiment of such Sn dopant sources relates to a tin-containing dopant composition having the general formula $R_nSnX_{4-n}$ where n=1 to 3, R is a functional group containing at least carbon (C) or hydrogen (H) and X is a halogen including F, Cl, Br or I. By way of example, a representative molecule is $CH_3SnF_3$. The molecule has a predicted vapor pressure of 1280 Torr and is stable at 25° C., both of which render it deliverable to the arc chamber via standard fluid delivery equipment including, but not limited to, flow lines and other conduit, valves and flow controllers. $CH_3SnF_3$ contains hydrogen, carbon, and fluorine atoms in its composition. Fluorine atoms in the Sn dopant source when ionized act as an etchant and can remove deposits in the chamber from C atoms or from residual gases present in the ion source chamber. However, an excess of F ions in the system can propagate the so-called "halogen cycle" and shorten the lifetime of the arc chamber. During the "halogen cycle", halogen ions in excess can cause etching of the W chamber walls onto the cathode. The deposition of W increases the operating voltage of the ion source which in turn increases the deposition of W until the ion source eventually breaks down. This ultimately shortens the lifetime of the ion source.

In an alternative embodiment, the Sn containing dopant source has a representative formula $R_nSnX_{4-n}$ where n=0 to 4, R is a functional group comprising carbon (C) and/or hydrogen (H) and X is a halogen selected from the group consisting of F, Cl, Br and I.

To offset ion source degradation, the H atoms incorporated into the Sn dopant compound provide a source of H ions during implantation which can neutralize halogen ions and reduce the damage by etching of the chamber walls.

To impart stability, the presence of C directly bonded to Sn, as opposed to H directly bonded to Sn, can reduce chemical degradation and decomposition of the compound during storage and delivery to the ion source chamber.

Without being bound by any particular theory, the carbon chain is deliberately limited in size, as an excessive number of C atoms and long hydrocarbon chains in the dopant source may lead to unwanted C deposition in the chamber. In comparison to smaller ions, longer hydrocarbon chains in ion implantation lead to larger ions which have a higher probability of recombining and reducing the so-called benefit of "total ionization cross section". Details for utilizing "total ionization cross section" as a benefit for ion implantation are described in Applicants co-pending U.S. Published Application No. 2015/0248992, the contents of which are hereby incorporated by reference in their entirety. Exemplary molecules of $R_nSnX_{4-n}$ to use in ion implantation have short hydrocarbon chains (e.g., 1-5 C atoms), as the R group, to reduce the probability of ion recombination. Additionally, such molecules have halogen ions to remove deposits C and other deposits in the system; and a sufficient number of H atoms to alleviate etching of the filament and chamber walls by halogen ions.

Figure 5:
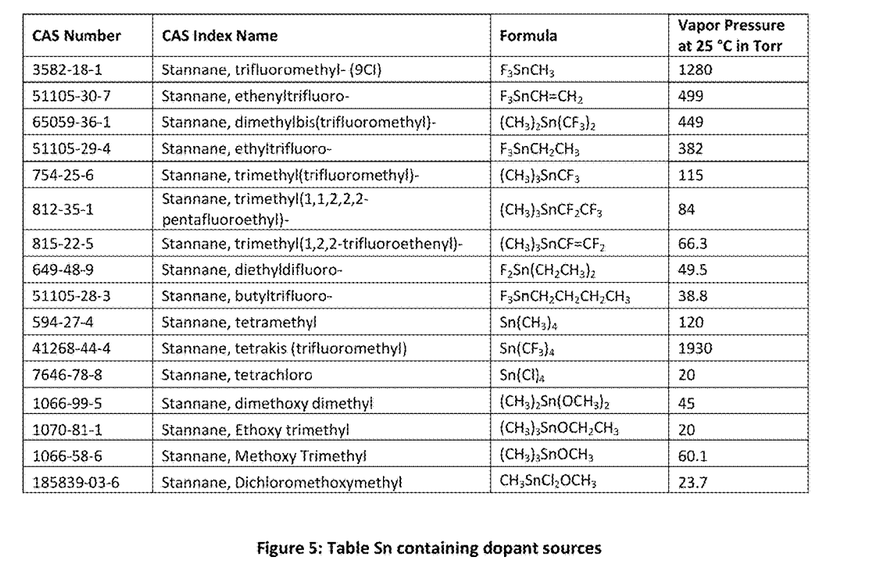
FIG. 5 is a table of Sn containing dopant sources in accordance with the principles of the present invention.

Other examples of compounds represented by $R_nSnX_{4-n}$, are $CH_3CH_2SnF_3$ and $CH_2=CHSnF_3$, both of which are listed in FIG. 5.

The Sn-molecules contemplated by the present invention have suitable bond energies for use in ion implant systems. Bond energy is a metric in determining the stability of dopant sources for use in ion implantation. Generally speaking, the bond energy is the energy required to break a bond between two atoms in a molecule. If the bond energies between atoms in the molecule are too low, the molecule can be unstable and can decompose at low (e.g., ambient) temperatures. For example, as the energy of the Sn—H bond in $SnH_4$ is relatively low at 264 kJ/mol, $SnH_4$ can decompose at 25° C., thereby rendering it not stable for storage and delivery in ion implantation. Conversely, if the bond energy is too high, the bonds may not be susceptible to breakage and, as a result, a sufficient ion beam for the dopant will not be generated. For example, as the energy of the Sn—F bond in $SnF_4$ is relatively high, at roughly 467 kJ/mol, $SnF_4$ is a solid and not suitable for ion implantation. The present invention has identified the need to create molecules having a bond energy above those of $SnH_4$ and below those of $SnF_4$. In this regard, and in accordance with the principles of the present invention, molecules are created which incorporate a certain number of Sn—C bonds with a certain number of Sn—F bonds to engineer a Sn-containing dopant source conducive for ion implantation. As such, the Sn compounds described herein are characterized by bond energies that are high enough so that the compound is stable at 25° C., but yet low enough to allow cleavage of the bonds so as to produce a sufficient number of Sn ions for use in ion implantation.

The ionization energy is another important parameter of dopant sources for ion implantation. A molecule with a low ionization energy will ionize and form a plasma at a lower operating voltage which can increase the probability of forming the desired dopant ion and can increase the ion source lifetime. The Sn compounds described herein possess ionization energies suitable for use in ion implantation, whereby ionization readily occurs to form a plasma which can increase the probability of forming the desired dopant Sn ions.

A second embodiment of Sn dopant sources for use in ion implantation relates to Sn-containing dopant composition having the general formula $R_nSnX_{4-n}$ where n=0 or 4, R is a functional group containing carbon (C) and/or hydrogen (H) and X is a halogen (F, Cl, Br, I). Two examples of these compounds are $Sn(CH_3)_4$ and $SnCl_4$. Both of these compounds are stable at 25° C. and $SnCl_4$ has a vapor pressure of 20 Torr and $Sn(CH_3)_4$ has a vapor pressure of 120 Torr at 25° C. as listed in FIG. 5. These compounds are preferably mixed with other gas species prior to ionization such that the total gas composition includes Sn, H, and a halogen atom.

A third embodiment of Sn dopant sources relates to compounds of the form $R_nSn(C_yX_z)_{4-n}$ where n=1 to 3; X is a halogen (X=F, Cl, Br, I); R contains a mixture of C and/or H atoms; and the values of y and z can vary depending on the C—C bonding. In particular, the values of y and z are such that each atom in the $C_yX_z$ group has a closed shell of valence electrons. For example, if y=2 and the two C atoms are single bonded C—C, then z=5. If y=2 and the two C atoms are double bonded together C═C, then z=3. Such compounds exhibit stability at room temperature, and exhibit a vapor pressure sufficient for ion implantation. By way of example, $(CH_3)_3SnCF_3$ is a liquid at room temperature with a predicted vapor pressure of 115 Torr. Other compounds of this type include $(CH_3)_2Sn(CF_3)_2$ and $(CH_3)_3SnC_2F_5$, both which are listed in FIG. 5.

In an alternative embodiment, compounds of the form $R_nSn(C_yX_z)_{4-n}$ may be suitable, where n=0 to 4; X is a halogen (X=F, Cl, Br, I); R contains a mixture of C and/or H atoms; and the values of y and z vary depending on the C—C bonding.

In a fourth embodiment, compounds of the form $R_nSn(C_yX_z)_{4-n}$ may be suitable, where n=0 or 4; X is a halogen (X=F, Cl, Br, I); R contains a mixture of C and/or H atoms; and the values of y and z vary depending on the C—C bonding. In particular, the values of y and z are such that each atom in the $C_yX_z$ group has a closed shell of valence electrons. For example, if y=2 and the two C atoms are single bonded C—C, then z=5. If y=2 and the two C atoms are double bonded together C═C, then z=3. For example, $Sn(CF_3)_4$ as listed in FIG. 5 has a vapor pressure of 1930 Torr and does not decompose at 25° C. These compounds are preferably mixed with other species prior to ionization such that the total gas composition includes Sn, H, and a halogen atom.

Figure 1:
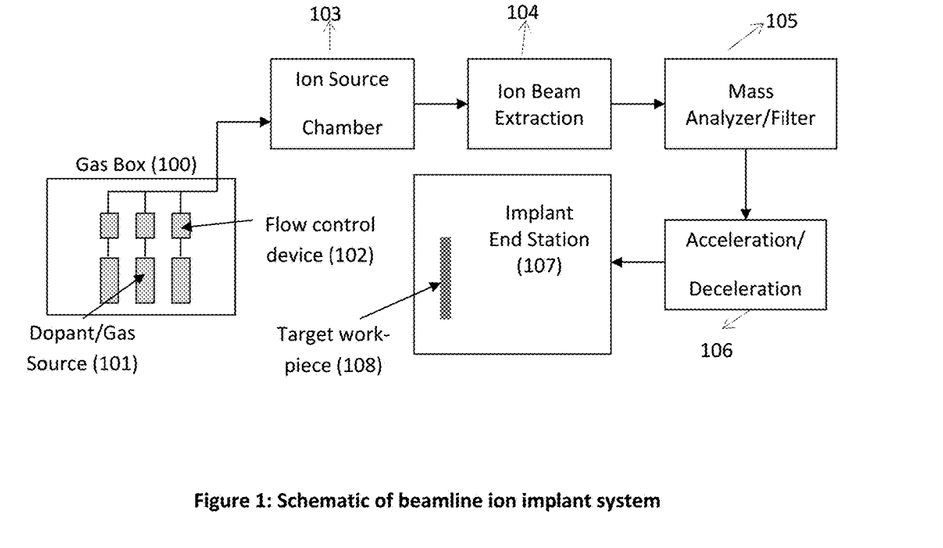
FIG. 1 is a schematic of a beamline ion implant system for implanting Sn in accordance with the principles of the present invention.

Another aspect of the disclosure relates to ion implantation methods which can be carried out using the compounds of the present invention. One exemplary method is a beam line ion implantation system. A generalized schematic of such a beam line ion implantation system is shown in FIG. 1. The Sn dopant source in a container with vacuum actuated check valve can be connected to a beam line ion implantation system shown in FIG. 1, or a plasma immersion ion implantation system shown in FIG. 2, discussed below.

Referring to FIG. 1, a dopant source material 101, e.g., gas, is used that contains the desired dopant element. Referring to FIG. 1, the gas is introduced into an ion source chamber 103, i.e., ionization chamber, and energy is introduced into the chamber to ionize the gas. Flow control device 102 which includes mass flow controllers and valves is used to control the flow of gas at a desired value. The ionization creates ions that contain the dopant element. An ion extraction system 104 is used to extract the ions from the ion source chamber in the form of an ion beam of desired energy. Extraction can be carried out by applying a high voltage across extraction electrodes. The beam is transported through a mass analyzer/filter 105 to select the species to be implanted. The ion beam can then be accelerated/decelerated 106 and transported to the surface of a target workpiece 108 positioned in an end station 107 for implantation of the dopant element into the workpiece 108. The workpiece may be, for example, a semiconductor wafer or similar target object requiring ion implantation. The ions of the beam collide with and penetrate the surface of the workpiece to form a region with the desired electrical and physical properties. It should be understood that variations to the method for beam line ion implantation are contemplated.

Figure 2:
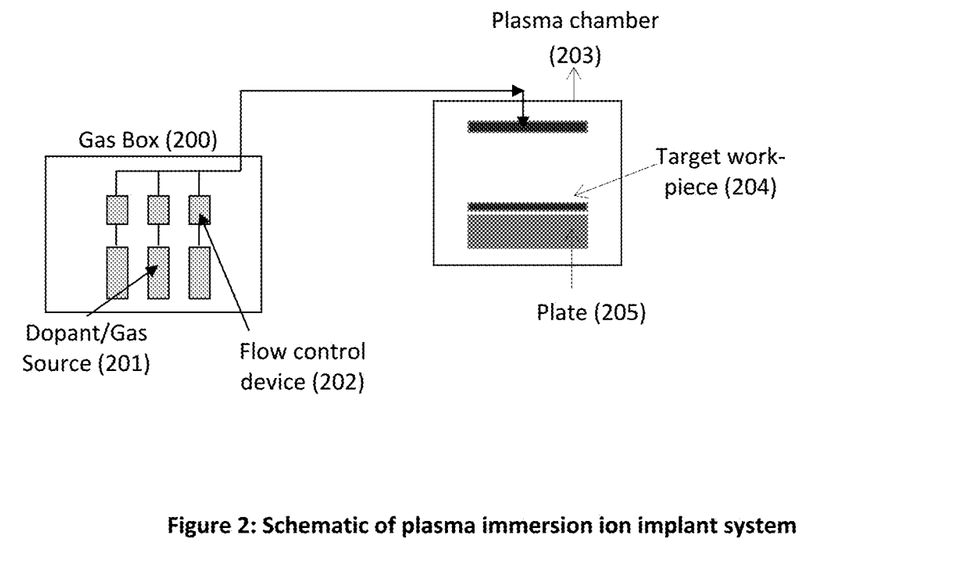
FIG. 2 is a schematic of a plasma immersion system for implanting Sn in accordance with the principles of the present invention.

Another exemplary ion implantation method which can be carried out using the compounds of the present invention is a plasma immersion ion implant (PIII) system. A generalized schematic of a PIII system is shown in FIG. 2. Such a system also consists of gas box 200 which is very similar to configuration and operation as 100. The gases are introduced into the plasma chamber 203. Energy is provided to generate and ionize the gas species. All of the ions present in the plasma are accelerated towards the target work piece 204. It should be understood that variations to the PIII method are contemplated.

Figures 3A, 3B:
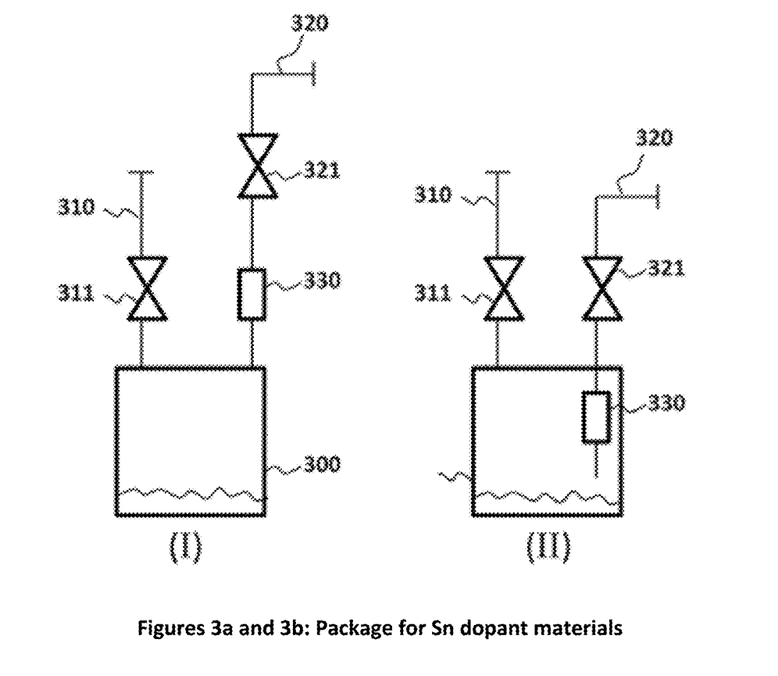
FIGS. 3a and 3b illustrate representative storage and delivery packages for the Sn dopant sources in accordance with the principles of the present invention.

Another aspect of the disclosure relates to storage and delivery of the Sn compositions. In one embodiment, the molecules can be stored and delivered from a container which is equipped with a vacuum actuated check valve to enable a sub-atmospheric delivery as shown in FIGS. 3a and 3b. The Sn dopant material is contained within a container 300. The container is equipped with an inlet port 310 to allow filling of container 300 with the desired dopant material. This port can also be used to purge the interior of container 300 with inert gas and evacuate container 300 before filling with dopant material. An outlet port 320 is provided to draw the material out of container 300. A vacuum actuated check valve 330 is provided upstream of outlet port. This vacuum actuated check valve enhances the safety while handling such Sn dopant material. In the scenario the user opens valve 321 to atmosphere, check valve 330 prevents introduction of any air or other contaminant inside container 300 and hence mitigate the risk fire while using pyrophoric dopant materials. The check valve 330 can be either installed outside 300 (Case I of FIG. 3a) or be installed inside container 300 (Case II of FIG. 3b).

Figure 4A:
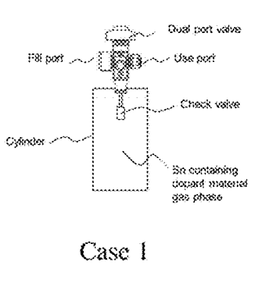
FIGS. 4a, 4b and 4c illustrate separate states of the Sn dopant sources in storage and delivery packages.
Figure 4B:
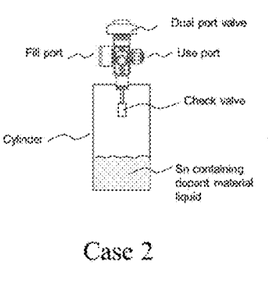
Figure 4C:
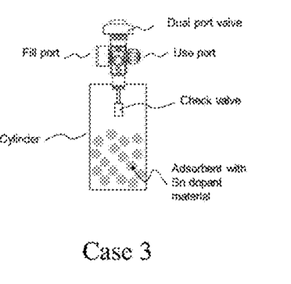

Representative schematics of a particular storage and delivery system with a particular state of Sn dopant material are illustrated in FIGS. 4a, 4b and 4c. This delivery system includes a container for holding the tin dopant material; a dual port valve assembly mechanically connected to the container with a fill port valve; and a discharge port valve. The fill port valve is in contact with the inside of the container and is configured to fill the container with a tin containing dopant material. The discharge port is in contact with a flow discharge path capable of introducing the dopant material from inside the container to an area outside of the container; and a check valve is configured to move from a closed position to an open position when a sub-atmospheric environment is present along the flow discharge path. Further detail of sub-atmospheric storage and delivery systems can be found in Applicants' U.S. Pat. Nos. 7,708,028; 7,905,247; 5,937,895; 6,007,609; 6,045,115; and 6,959,724; and U.S. application Ser. No. 14/638,397, the respective disclosures of which are hereby incorporated by reference in their entireties, for all purposes. The Sn dopant source can be in the gas phase (Case 1 of FIG. 4a); a liquid phase in equilibrium with the gas phase wherein the vapor pressure is high enough to allow flow from the discharge port (Case 2 of FIG. 4b); or an adsorbed state on a solid media (Case 3 of FIG. 4c).

Another aspect of the disclosure relates to modifications for improving the ion implantation performance of Sn. For example, any of the Sn dopant sources as disclosed hereinbefore can be used with a diluent species. Representative formulas of diluent species include but are not limited to $SnR_4$, $X_2$, $SnX_4$, $H_2$ and $CH_4$ where R is one or multiple different groups comprising C and/or H; and X is a halogen (X=F, Cl, Br, I) or a mixture of halogen species. The diluent species may either be mixed in the same container as the dopant source or be located in a separate container and co-flown with the Sn dopant source. Suitable diluent species include $SnCl_4$, $Sn(CH_3)_4$, $F_2$, and $Cl_2$. Inert gases can also be co-flown with any of the gases and gas mixtures mentioned above to improve the performance of the ion implantation process. Gases such as $N_2$, He, Ne, Ar, Kr, and Xe can add stability to gases and can sometimes ionize and sputter unwanted deposits from the walls or components of the chamber thereby increasing the operation time for the ion implanter. The diluent species can contribute H, Sn, or halogen atoms to the gas mixture and the flow rate can be controlled to obtain a specific flow rate or flow range at which optimal ionization cross sectional benefits can be attained. Further, the R group in $SnR_4$ is preferably a short hydrocarbon chain of 1-5 carbons, because, as the size of the R group increases, the vapor pressure tends to decrease below acceptable limits for certain ion implantation processes, and the probability of recombinative ionization increases.

In accordance with the principles of the present invention and in one preferred aspect of the present invention, Sn-containing species as disclosed herein are selected to exhibit certain attributes conducive for carrying out Sn ion implantation processes shown in FIG. 1 and FIG. 2. In one example, the selected Sn-containing species for certain ion implantation processes have a sufficient vapor pressure at 25° C. to allow flow from a storage and delivery device into an ion chamber that is operably connected to said storage and delivery device. In another example, Sn-containing species as disclosed herein can be used to carry out the processes of FIG. 1 or FIG. 2, whereby the Sn-containing species has one or more of the following attributes: (i) chemical stability during storage and delivery; (ii) naturally occurring as a liquid at room temperature; (iii) sufficient vapor pressure for delivery and processing in an ion implantation system; (iv) feasible synthesis routes; and (v) comprises Sn, H and a halogen atom.

In another embodiment of the present invention, compounds are contemplated with the representative formula $R_{4-y-z}Sn(OR')_y X_z$, where z=0 to 3, y=1 to 4, X is a halogen (X=F, Cl, Br, I) and R and R' contains a mixture of C and/or H atoms. Examples of such compounds include, but are not limited to, $(CH_3)_2Sn(OCH_3)_2$ with a predicted vapor pressure of 45 Torr; $(CH_3)_3SnOCH_2CH_3$ with a predicted vapor pressure of 20 Torr; $(CH_3)_3SnOCH_3$ with a predicted vapor pressure of 60.1 Torr; and $CH_3SnCl_2OCH_3$ with a predicted vapor pressure of 23.7 Torr. These compounds are preferably mixed with other species prior to ionization such that the total gas composition includes Sn, H, and a halogen atom.

There are several isotopes of Sn. The highest natural abundance of Sn isotopes are $^{120}Sn$ at 32.85%, $^{118}Sn$ at 24.03%, and $^{116}Sn$ at 14.3%. Enriching dopant sources to increase the abundance of an isotope over the natural abundance can improve the beam current for that said isotopic mass during ion implantation, and is contemplated by the present invention. It should be understood that reference to any and all of the Sn dopant species herein is intended to mean naturally occurring and isotopically enriched levels of any of its isotopes.

It should be understood that any the Sn dopant sources of the present invention can be used in conjunction with a physical adsorbent-based gas storage medium in a sub-atmospheric delivery system. In this type of absorbent-based system, the tin dopant source is held in a sorptive condition by a solid sorbent medium, which is present in the storage and dispensing container, and the tin species is desorptively released from the sorbent medium during the dispensing process. In a sub-atmospheric delivery system, reversibly adsorbing the gas onto a physical carrier adsorbent can reduce the pressure of the container compared to only storing the tin species in the gas phase and lower the pressure of the container to below atmosphere. The said solid phase adsorbent can be silica, carbon molecular sieves, activated carbon, zeolite, polymer based materials, and more. The form of adsorbent can be beads, granules, pellets, or monolithic forms like blocks and discs. Additionally, the adsorbent may include a metal organic framework as described in greater detail in U.S. Pat. Nos. 9,138,720 and 9,427,722; and U.S. Patent Publication Nos. 2016151762 and 2016160348, the disclosures of which are hereby incorporated by reference in their respective entireties. The bulk adsorbent typically can make up the majority of the storage and dispensing container, at least 60% of the interior volume of the container. The porosity of the adsorbent and the pore size distribution can be designed to best fit the requirements of the targeted tin dopant source. The adsorbent is preferably purified by suitable means as known in the art, and passivated before adsorbing the gas species.

With regards to an adsorbent-based system, the present invention recognizes that many Sn species, which may not meet the applicable stability criteria for use in Sn ion implantation, may be utilized with a suitable adsorbent, so as to improve the compound stability. By way of example, and not intended to be limiting, some tin halides and organotin hydrides are unstable and can decompose under ambient conditions, thereby not exhibiting applicable stability during delivery and storage as would be required for Sn ion implantation processes. Unstable tin halides can have the formula $X_{4-n}SnH_n$; and unstable organotin hydrides can have the formula $R_{4-n}SnH_n$, where n=1 to 3; X is a halogen; and R is a functional group containing carbon and/or hydrogen. Alternatively, unstable tin hydrides can have the formula $Sn_xH_{2x+2}$ where x=1 to 3. As the number of Sn—H bonds increases, these tin compounds are characterized by the absence of suitable stability required during storage and delivery for ion implantation processes. To offset such stability, the adsorbent can inhibit the decomposition of unstable compounds, and increase the storage capability of a gas cylinder. In this regard, the present invention recognizes that carbon based micro and meso-porous adsorbents, which have been used for storing hydrocarbons such as acetylene and methane, can be implemented herein as an adsorbent-based system for storage of and delivery of Sn species which may not otherwise exhibit stability criteria during storage and delivery for ion implantation processes. Details for implementing such an absorbent system are disclosed in U.S. Pat. No. 6,006,797, which is incorporated by reference herein in its entirety. By way of example, acetylene can decompose at pressure as low as 1.4 bar, but when dissolved in acetone and adsorbed onto a solid sorbent, the acetylene can be stored at greater than 18 bar.

While it has been shown and described what is considered to be certain embodiments of the invention, it will, of course, be understood that various modifications and changes in form or detail can readily be made without departing from the spirit and scope of the invention. It is, therefore, intended that this invention not be limited to the exact form and detail herein shown and described, nor to anything less than the whole of the invention herein disclosed and hereinafter claimed.

The invention claimed is:

1. A method for using Sn containing dopant material for an ion implantation process, comprising the steps of:
   storing a Sn containing dopant source in a storage and delivery container;
   the Sn-containing dopant source characterized by one or more of the following attributes: (i) stability during storage and delivery; (ii) a vapor pressure of greater than or equal to 20 Torr at room temperature (25° C.); (iii) existing as a liquid at room temperature; and (iv) comprising Sn, H and a halogen atom;
   withdrawing the Sn containing dopant source in the vapor phase from the storage and delivery container when a diaphragm moves a vacuum actuated check valve from a closed position to an open position in response to a sub-atmospheric condition achieved along the discharge flow path;
   flowing the vaporized the Sn containing dopant source in response to the sub-atmospheric condition achieved along the discharge flow path; and
   introducing the Sn-containing dopant source vapor to an ion source chamber.

2. The method of claim 1, wherein said Sn containing dopant source has a representative formula $R_nSnX_{4-n}$ where n=0 to 4, R is a functional group comprising carbon (C) and/or hydrogen (H) and X is a halogen selected from the group consisting of F, Cl, Br and I.

3. The method of claim 1, wherein said Sn-containing dopant source has a representative formula $R_nSnX_{4-n}$ where n=1 to 3, R is a functional group comprising carbon (C) and/or hydrogen (H) and X is a halogen selected from the group consisting of F, Cl, Br and I.

4. The method of claim 1, wherein said Sn-containing dopant source has a representative formula $R_nSnX_{4-n}$ where n=0 or 4, R is a functional group comprising carbon (C) and/or hydrogen (H) and X is a halogen selected from the group consisting of F, Cl, Br and I.

5. The method of claim 1, wherein the Sn-containing dopant source has the representative formula $R_nSn(C_yX_z)_{4-n}$ where n=1 to 3, X is a halogen selected from the group consisting of F, Cl, Br and I, and R comprises C and/or H atoms, and the values of y and z vary depending on the C—C bonding such that each atom in the $C_yX_z$ group has a closed shell of valence electrons.

6. The method of claim 1, wherein the Sn-containing dopant source has the representative formula $R_nSn(C_yX_z)_{4-n}$ where n=0 or 4, X is a halogen selected from the group consisting of F, Cl, Br and I and R comprises C and/or H atoms, and the values of y and z vary depending on the C—C bonding such that each atom in the $C_yX_z$ group has a closed shell of valence electrons.

7. The method of claim 1, wherein the Sn-containing dopant source material has the representative formula $R_{4-y-z}Sn(OR')_yX_z$ where z=0 to 3, y=1 to 4, X is a halogen (X=F, Cl, Br, I) and R and R' contains a mixture of C and/or H atoms.

8. The method of claim 1, further comprising introducing a diluent species into the ion source chamber.

9. A source supply for a Sn dopant gas composition comprising:
   a Sn-containing dopant source characterized by one or more of the following attributes: (i) stability during storage and delivery; (ii) a vapor pressure of greater than or equal to 20 Torr at room temperature (25° C.); (iii) existing as a liquid at room temperature; and (iv) comprising Sn, H and a halogen atom;
   a delivery and storage device for maintaining the Sn-containing dopant source in a pressurized state within an interior volume of the device, said delivery device in fluid communication with a discharge flow path, wherein said delivery device comprises a vacuum actuated check valve that is actuated by a diaphragm to allow a controlled flow of the Sn-containing dopant source from the interior volume of the device in response to a sub-atmospheric condition achieved along the discharge flow path.

10. The source supply of claim 9, said delivery and storage device comprises an adsorbent onto which said Sn-containing dopant source is adsorbed thereon during storage.

11. The source supply of claim 9, wherein said Sn-containing dopant source is stored in the delivery and storage device in a gas phase.

12. The source supply of claim 9, wherein said Sn-containing dopant source is stored in the delivery and storage device in a liquid phase in equilibrium with a gas phase, wherein said Sn-containing dopant source exerts a sufficient vapor pressure to allow flow from the storage and delivery device into an ion chamber that is operably connected to said storage and delivery device.

13. A Sn-containing dopant composition for use in an ion implantation process, comprising:
   a Sn-containing dopant source material characterized by the following attribute: (i) a vapor pressure of greater than or equal to 20 Torr at room temperature (25° C.); and
   a delivery and storage device for maintaining the Sn-containing dopant source material in a pressurized state within an interior volume of the device, said delivery device in fluid communication with a discharge flow path, wherein said delivery device comprises a vacuum actuated check valve that is actuated by a diaphragm to allow a controlled flow of the Sn-containing dopant source material from the interior volume of the device in response to a sub-atmospheric condition achieved along the discharge flow path.

14. The Sn-containing dopant composition of claim 13, further characterized by one or more of any of the following attributes: (ii) stability during storage and delivery; and (iii) existing as a liquid at room temperature; and (iv) comprising Sn, H and a halogen atom.

15. The Sn-containing dopant composition of claim 14, further characterized by 2 or more of the attributes of (ii), (iii) and (iv).

16. The Sn-containing dopant composition of claim 13, further comprising each of attributes (i), (ii), (iii), and (iv).

17. The Sn-containing dopant composition of claim 13, wherein said Sn containing dopant source material has a representative formula $R_nSnX_{4-n}$ where n=0 to 4, R is a functional group containing carbon (C) and/or hydrogen (H); and X is a halogen selected from the group consisting of F, Cl, Br and I.

18. The Sn-containing dopant composition of claim 13, wherein said Sn-containing dopant source material has a representative formula $R_nSnX_{4-n}$ where n=1 to 3, R is a functional group comprising carbon (C) and/or hydrogen (H); and X is a halogen selected from the group consisting of F, Cl, Br and I.

19. The Sn-containing dopant composition of claim 13, wherein said Sn-containing dopant source material has a representative formula $R_nSnX_{4-n}$ where n=0 or 4, R is a functional group comprising carbon (C) and/or hydrogen (H); and X is a halogen selected from the group consisting of F, Cl, Br and I.

20. The Sn-containing dopant composition of claim 13, wherein the Sn-containing dopant source material has the representative formula $R_nSn(C_yX_z)_{4-n}$ where n=1 to 3, X is a halogen selected from the group comprising of F, Cl, Br and I; and R comprises C and/or H atoms, and the values of y and z vary depending on the C—C bonding such that each atom in the $C_yX_z$ group has a closed shell of valence electrons.

21. The Sn-containing dopant composition of claim 13, wherein the Sn-containing dopant source material has the representative formula $R_nSn(C_yX_z)_{4-n}$ where n=0 or 4, X is a halogen selected from the group consisting of F, Cl, Br and I, R comprises C and/or H atoms, and the values of y and z vary depending on the C—C bonding such that each atom in the $C_yX_z$ group has a closed shell of valence electrons.

22. The Sn-containing dopant composition of claim 13, wherein the Sn-containing dopant source material has the representative formula $R_{4-y-z}Sn(OR')_yX_z$ where z=0 to 3, y=1 to 4, X is a halogen (X=F, Cl, Br, I) and R and R' contains a mixture of C and/or H atoms.

23. The Sn-containing dopant composition of claim 13, wherein said Sn-containing dopant composition is selected from the group consisting of $F_3SnCH_3$, $F_3SnCH=CH_2$, $(CH_3)_2Sn(CF_3)_2$, $F_3SnCH_2CH_3$, $(CH_3)_3SnCF_3$, $(CH_3)_3SnCF_2CF_3$, $(CH_3)_3SnCF=CF_2$, $F_2Sn(CH_2CH_3)_2$, $F_3SnCH_2CH_2CH_2CH_3$, $Sn(CH_3)_4$, $Sn(CF_3)_4$ and $Sn(Cl)_4$.

24. The Sn-containing dopant composition of claim 13, wherein said Sn-containing dopant source material is selected from the group consisting of $F_3SnCH_3$, $F_3SnCH=CH_2$, $(CH_3)_2Sn(CF_3)_2$, $F_3SnCH_2CH_3$, $(CH_3)_3SnCF_3$, $(CH_3)_3SnCF_2CF_3$, $(CH_3)_3SnCF=CF_2$, $F_2Sn(CH_2CH_3)_2$, $F_3SnCH_2CH_2CH_2CH_3$.

25. The Sn-containing dopant composition of claim 13, wherein said Sn-containing dopant source material is utilized in combination with an adsorbent-based system, and further wherein said Sn-containing dopant source material is characterized by the absence of attribute (i).

26. The method of claim 1, wherein the Sn-containing dopant source has the representative formula $R_nSn(C_yX_z)_{4-n}$ where n=0 to 4, X is a halogen selected from the group consisting of F, Cl, Br and I, and R comprises C and/or H atoms, and the values of y and z vary depending on the C—C bonding such that each atom in the $C_yX_z$ group has a closed shell of valence electrons.

* * * * *